US00PP22603P2

(12) United States Plant Patent
Zaiger et al.

(10) Patent No.: US PP22,603 P2
(45) Date of Patent: Mar. 27, 2012

(54) CHERRY TREE NAMED 'ROYAL ELAINE'

(50) Latin Name: *Prunus avium*
Varietal Denomination: Royal Elaine

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/925,759

(22) Filed: Oct. 29, 2010

(51) Int. Cl.
*A01H 5/00* (2006.01)

(52) U.S. Cl. ..... Plt./181

(58) Field of Classification Search ..... Plt./181
See application file for complete search history.

*Primary Examiner* — Susan McCormick Ewoldt

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with an attractive red skin color.
2. Regular and heavy production of medium to large size fruit.
3. Fruit with good flavor and eating quality.
4. Firm fruit with good handling and shipping qualities.
5. Vigorous, upright tree growth.

1 Drawing Sheet

Botanical classification: *Prunus avium.*

STATEMENT REGARDING FEDERALLY SPONSORED RESEARCH AND DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Bing' Cherry (non-patented) and the proprietary selections '17H177' and '49G1093'.

ORIGIN OF THE VARIETY

The present new variety of cherry tree (*Prunus avium*) was originated by us in our experimental orchard located near Modesto, Calif. from an open pollinated seedling selection with the field identification number '17H177'. The seed parent (17H177) originated from an open pollinated proprietary seedling '49G1093', which originated from a group of open pollinated seedlings of 'Bing' Cherry (non-patented). A large group of these open pollinated seedlings were budded on established 'Mahaleb' Rootstock (non-patented) to accelerate fruit production and maintained under close and careful observation. One such seedling, which is the present variety, exhibited desirable fruit and tree characteristics and was selected in 1986 for asexual reproduction and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of cherry tree is of large size, vigorous, upright growth and a regular and productive bearer of large size fruit with good flavor and eating quality. The fruit is further characterized by its attractive red skin color and firm flesh. In comparison to its immediate seed parent (17H177) the fruit of the new variety is larger in size, firmer and ripens approximately 6 days later. In comparison to its ancestor 'Bing' Cherry (non-patented) the fruit matures in the same season with larger size, is less susceptible to rain cracking, fruit doubling and spurs.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 20 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 20 year old specimens grown near Modesto, Calif., with color in accordance with Munsell Book of color.

Tree:

*Size*.—Large. Tree pruned to 3 to 4 meters in height and width for economical harvesting of fruit.

*Vigor*.—Vigorous, tree growth reaching 1 to 2 meters the first growing season. Growth rate varies slightly with soil type and depth, cultural practices and climatic conditions.

*Form*.—Upright. During the first and second growing seasons, scaffolds are selected and tied down to increase crotch angle and help tree spread to desired width of 3 to 4 meters.

*Branching habit*.—Semi-spreading, crotch angle approximately 60°, heavy fruit production tends to increase branch angles.

*Productivity*.—Productive, produces heavy crop annually.

*Bearer*.—Regular, adequate fruit set 16 consecutive years.

*Fertility*.—Self-sterile, pollinator required.

*Density*.—Medium dense, usually pruned to vase shape to allow more sunlight to center of tree to enhance health of fruit spurs and fruit color.

*Hardiness*.—Hardy in all stone fruit growing areas of California. Tree gown in USDA Hardiness Zone 9. Winter chilling requirement approximately 850 hours at or below 45° F.

Trunk:

*Size*.—Large. Measured 91.4 cm in circumference at 35.6 cm above ground on a 20 year old tree.

*Stocky*.—Medium stocky.

*Texture*.—Medium rough, roughness increases with age of tree.

*Color*.—Varies from 10YR 4/2 to 2.5Y 4/2.

Branches:

*Size*.—Medium. Average circumference 20.8 cm at 1.2 meters above ground on a 20 year old tree.

*Surface texture*.—New growth relatively smooth. Mature growth medium rough, roughness increases with age.

*Lenticels*.—Average number 16 in a 25.8 sq cm section. Average length 5.9 mm. Average width 2.1 mm. Color varies from 7.5YR 5/8 to 10YR 5/10.

*Color*.—New growth varies from 2.5GY 5/8 to 5GY 5/8. Old growth 2.5Y 5/2, varies with age of growth.

Leaves:

*Size*.—Large. Average length 139.8 mm. Average width 67.6 mm.

*Form*.—Elliptical.

*Apex*.—Acuminate.

*Base*.—Cuneate.

*Margin*.—Doubly serrate.

*Thickness*.—Medium.

*Surface texture*.—Upper surface relatively smooth, slight indentations over leaf veins, glabrous. Lower surface relatively smooth, slight ridges created by midrib and pinnate venation, glabrous.

*Petiole*.—Average length 34.1 mm. Average width 2.1 mm. Longitudinally grooved. Color varies from 5GY 5/4 to 7.5GY 4/4. Surface — glabrous.

*Glands*.—Type — reniform. Size — large. Average length 2.1 mm. Average width 1.2 mm. Average number 4, varies from 2 to 6. Located primarily on upper portion of petiole. Color varies from 10R 4/10 to 10Y 6/6.

*Stipules*.—Average number at base of leaf blade — 2. Average length 3.8 mm. Margin — ciliate. Color 2.5GY 6/6.

*Color*.—Upper surface varies from 7.5GY 2/2 to 7.5GY 2/4. Lower surface varies from 7.5GY 4/2 to 7.5GY 4/4. Midvein color varies from 2.5GY 6/6 to 5GY 6/6.

Flower buds:

*Size*.—Medium to large. Average length 16.7 mm. Average diameter 9.6 mm.

*Hardiness*.—Hardy with respect to California winters.

*Form*.—Plump, conical, becoming elongated before opening.

*Pedicel*.—Average length 10.8 mm. Average width 1.0 mm. Color varies from 2.5GY 5/8 to 5GY 5/5.

*Color*.—N 9.5/(white).

*Number of buds per spur*.—Average number 5, varies from 3 to 9.

Flowers:

*Blooming period*.—Date of First Bloom Mar. 16, 2010. Date of Petal Fall Mar. 26, 2010, varies slightly with climatic conditions.

*Size*.—Medium to large. Average height 17.9 mm. Average diameter 32.7 mm.

*Petals*.—Normally 5, alternately arranged to sepals. Form — nearly orbicular, narrows at point of attachment. Average length 16.7 mm. Average width 17.4 mm. Margin — sinuate. Color — both upper and lower surfaces N 9.5/(white). Both upper and lower surfaces glabrous.

*Sepals*.—Normally 5, alternately arranged to petals. Average length 6.6 mm. Average width 4.7 mm. Shape — triangular. Margin — entire. Both upper and lower surfaces glabrous. Color — upper surface varies from 5GY 6/6 to 5GY 5/8. Lower surface varies from 5GY 5/8 to 7.5R 3/6.

*Stamens*.—Average number 34. Average filament length 11.6 mm. Filament color N 9.5/(white). Anther color varies from 5Y 8/8 to 5Y 8/10.

*Pollen*.—Self sterile, pollinator required. Color varies from 2.5Y 7/10 to 5Y 7/12.

*Pistil*.—Normally one. Surface — glabrous. Average length 13.6 mm. Position of stigma average of 1.6 mm below anthers. Color varies from 2.5GY 7/6 to 2.5GY 7/8.

*Fragrance*.—Very slight.

*Color*.—N 9.5/(white).

*Number flowers per flower bud*.—Average 3, varies from 1 to 4.

*Pedicel*.—Average length 14.8 mm. Average width 1.2 mm. Color varies from 5 GY 5/8 to 7.5R 3/6.

Fruit:

*Maturity when described*.—Firm ripe.

*Date of first picking*.—May 22, 2010.

*Date of last picking*.—May 30, varies slightly with climatic conditions.

*Size*.—Medium to large. Average diameter axially 26.9 mm. Average transversely in suture plane 29.0 mm.

Average weight 14.2 grams, varies slightly with fertility of the soil, amount of thinning and climatic conditions.

*Form*.—Nearly globose, slightly flattened at apex and base.

*Suture*.—Nearly smooth, extends from base to apex.

*Ventral surface*.—Nearly smooth to very slightly lipped.

*Apex*.—Slightly retuse.

*Base*.—Varies from slightly flat to retuse.

*Stem cavity*.—Rounded to slightly elongated in suture plane. Average depth 1.7 mm. Average diameter 3.8 mm.

Stem:

*Size*.—Medium to large. Average length 37.0 mm. Average diameter 1.4 mm.

*Color*.—Varies from 5GY 6/4 to 7.5GY 6/4.

Flesh:

*Ripens*.—Evenly.

*Texture*.—Firm.

*Fibers*.—Few, small, tender.

*Firmness*.—Firm, comparable to 'Bing' Cherry (non-patented).

*Aroma*.—Moderate.

*Amydgalin*.—Undetected.

*Eating quality*.—Good.

*Flavor*.—Good, good balance between acid and sugar.

*Juice*.—Very juicy, enhances flavor.

*Brix*.—Average 20.5°, varies slightly with amount of fruit per tree and climatic conditions.

*Color*.—Varies from 5R 3/8 to 7.5R 2/6. Pit cavity 7.5R 3/6 to 7.5R 2/6.

Skin:

*Thickness*.—Medium.

*Surface*.—Smooth.

*Pubescence*.—Wanting.

*Tendency to crack*.—None during dry weather. Only slight tendency to crack in wet weather, depends on stage of maturity.

*Color*.—Color varies from 7.5R 2/4 to 7.5R 2/6.

*Tenacity*.—Tenacious to flesh.

*Astringency*.—Slight to none.

Stone:

*Type*.—Clingstone.

*Size*.—Medium. Average length 12.6 mm. Average width 10.8 mm. Average thickness 8.5 mm.

*Form*.—Ovoid.

*Base*.—Flat.

*Apex*.—Rounded.

*Surface*.—Relatively smooth, except for ridges near the suture.

*Sides*.—Equal to unequal. Some stones have one side extending further from suture plane.

*Ridges*.—A small, narrow ridge on each side of suture extending from base to apex.

*Tendency to split*.—None.

*Color*.—10YR 6/6, when dry.

Kernel:

*Form*.—Ovate.

*Viability*.—Viable, good embryo development.

*Size*.—Small. Average length 7.9 mm. Average width 5.8 mm. Average depth 3.4 mm.

*Skin color*.—Varies from 5Y 9/2 to 5Y 9/4.

Use:

*Dessert*.—Market — local and long distance.

Keeping quality: Good, held firm for 14 days in cold storage at 38° to 42° F. and maintained good appearance and eating quality.

Shipping quality: Good, showed minimal bruising or scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree (*Prunus avium*), substantially as illustrated and described.

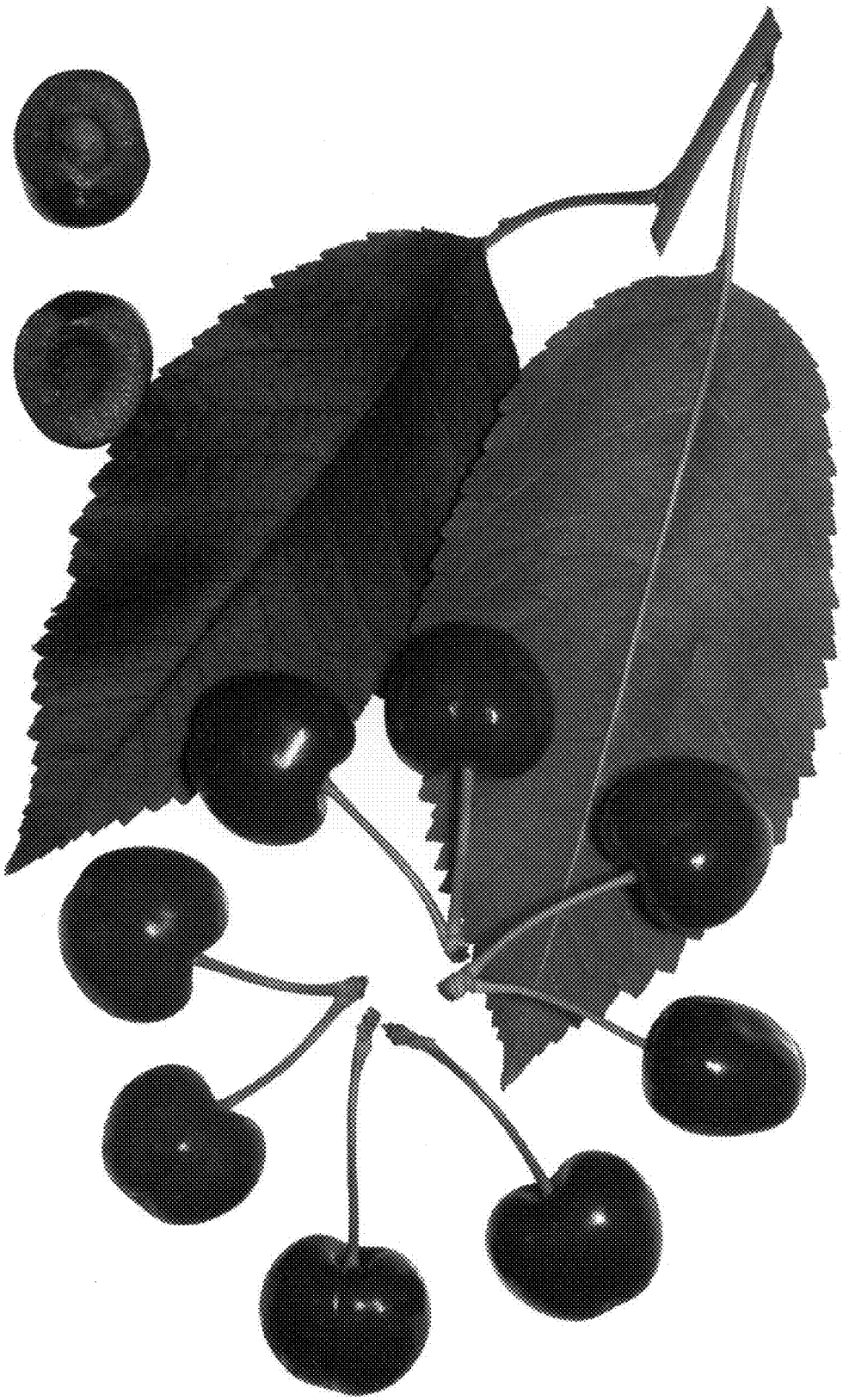

* * * * *